United States Patent [19]
Ellis et al.

[11] Patent Number: 6,083,490
[45] Date of Patent: Jul. 4, 2000

[54] UV ABSORBING COMPOSITIONS

[75] Inventors: David Graham Ellis, 4 William Street, Mount Waverley, Victoria, 3149; Michael Ary Bos, Pearcedale, both of Australia

[73] Assignees: M&J Consultants Pty Ltd; David Graham Ellis, both of Victoria, Australia

[21] Appl. No.: 09/068,290
[22] PCT Filed: Nov. 6, 1996
[86] PCT No.: PCT/AU96/00697
    § 371 Date: May 6, 1998
    § 102(e) Date: May 6, 1998
[87] PCT Pub. No.: WO97/17406
    PCT Pub. Date: May 15, 1997

[30] Foreign Application Priority Data
  Nov. 6, 1995 [AU] Australia ............... PO 6389
  May 28, 1996 [AU] Australia ............... PO 0095

[51] Int. Cl.$^7$ ................................. A61K 7/021
[52] U.S. Cl. ............... 424/59; 424/401; 424/67; 424/70.9; 424/614; 424/641; 424/642
[58] Field of Search ............... 424/451, 59, 67, 424/70.9, 614, 641, 642

[56] References Cited

U.S. PATENT DOCUMENTS

| | | | |
|---|---|---|---|
| 5,441,726 | 8/1995 | Mitchnick et al. | 424/59 |
| 5,468,471 | 11/1995 | Zecchino et al. | 424/59 |
| 5,573,753 | 11/1996 | Tapley | 424/59 |

FOREIGN PATENT DOCUMENTS

| | | |
|---|---|---|
| 0535971 A1 | 4/1993 | European Pat. Off. . |
| 0535972 A1 | 4/1993 | European Pat. Off. . |
| 0559319 A2 | 9/1993 | European Pat. Off. . |
| 2206339 | 1/1989 | United Kingdom . |
| 2226018 | 6/1990 | United Kingdom . |
| WO 94/18940 | 9/1994 | WIPO . |

*Primary Examiner*—Thurman K. Page
*Assistant Examiner*—Lakshmi Channavajjala
*Attorney, Agent, or Firm*—Wolf, Greenfield & Sacks, P.C.

[57] ABSTRACT

A process for producing a liquid dispersion of an inorganic oxide selected from zinc oxide, titanium dioxide and iron oxide, and having a particle size in the range of 0.02 to 30 $\mu$m, the process including comminuting the oxide in the presence of the liquid, the liquid being constituted by or including a component having available hydrogen and/or oxygen ions. The liquid is selected from one of an alcohol, ester, hydrogenated ester or polymer containing hydroxyl or hydrogen group(s). The stable dispersion which does not aggregate or agglomerate is suitable for use in topical preparations such as skin care or therapeutic products, cosmetics or hair care products.

17 Claims, 1 Drawing Sheet

UV ABSORBING COMPOSITIONS

FIELD OF THE INVENTION

The present invention relates to UV absorbing compositions, in particular to UV absorbing composition including a surface modified inorganic oxide dispersed in particulate form.

BACKGROUND OF THE INVENTION

The invention will be now specifically described in reference to the use of modified zinc oxide as the UV attenuating oxide, however the invention also extends to other inorganic oxides including titanium dioxide and Iron oxide.

Zinc oxide scatters some wavelengths of light and absorbs other selected wavelengths of light. It exhibits very strong absorption at wavelengths just short of the visible spectrum. It Is a strong UVB absorber at the 210–320 nm wavelength and also at the UVA 320–840 nm wavelength. At wavelengths longer than 370 nm. protection is provided by scattering and at wavelengths shorter than 370 nm, protection is achieved predominantly by absorption. Zinc oxide exhibits a strong semi-conductor absorption in the ultraviolet region. The optimum size of a zinc oxide particle for attenuation of the ultraviolet radiation is less than 0.06 $\mu$m for the wavelength range 300–400 nm. Absorption is the dominant mechanism for attenuation of ultraviolet radiation in the wavelength range of 300–400 nm.

Zinc oxide has been used as a white reflective pigment (particles size 1.0–20 $\mu$m) and as a UV absorber (particles 0.3–5 $\mu$m) for many years. The earliest form of presentation of zinc oxide as a sunscreen agent is a pigmented cream which is used to protect various parts of the exposed body, particularly the nose. Although this zinc oxide cream has its place, the conspicuous nature of the cream when on the skin reduces Its cosmetic appeal significantly. Attempts at turning a disadvantage to advantage has led to recent variations of the zinc oxide cream in which a coloured pigment is used to produce a brightly colour cream such as blue, red, yellow or green cream. Such modifications, although popular particularly with the young, have limited cosmetic appeal to the more general population.

It is highly desirable that the UV attenuating substance be invisible on the skin with any colour variation in the sunscreen formulation being adjusted to achieve a desired cosmetic effect.

To overcome this visual problem and also improve the performance as a sunscreen, zinc oxide with a particle size of 0.1–1.0 $\mu$m has been used in order to increase UV absorption and decrease reflectance of light. Moreover zinc oxide with a particle size less than 0.1 $\mu$m becomes invisible when rubbed onto the skin. However prior art attempts to use microfine zinc oxide has led to difficulties in formulation. The fine zinc oxide powder is difficult to keep in suspension. The particles irreversibly bond during manufacture, and when formulated into a dispersion, tend to aggregate, agglomerate and then settle out. Prior art sunscreen creams incorporating zinc oxide in this particle size range appear white on the skin, develop a settled out layer which is difficult to disperse. Moreover the prior art formulations tend to develop a clear top layer.

Prior art zinc oxide formulations are also limited in terms of the amount of zinc oxide that could be mixed into the formulation (up to about 10% by weight) which limits the blockout effect of the sunscreen. To disperse the zinc oxide in the formulation, various wetting agents, in combination with anti-settling agents have been used, this effectively decreasing the amount of UV active that can be included in the formulation, adding to the cost of manufacture and increasing the risk of an adverse skin reaction.

When zinc oxide is freshly made into a fine powder by burning fumed zinc metal vapour, oxygen will bond onto the fresh zinc oxide surfaces. This oxygen bonding then prevents any further bonding with hydrogen or oxygen ions when the zinc oxide comes in contact with an ester or alcohol and means that this zinc oxide is prone to agglomeration, aggregation, settling and hence whitening.

Furthermore, freshly made zinc oxide can absorb carbon dioxide which leads to the formation of carbonates on its surface. This absorption of carbon dioxide thus inhibits the UV absorbing properties of the zinc oxide.

SUMMARY OF THE INVENTION

We have surprisingly found that it is possible to produce a stable oxide containing product which is less prone to aggregation, agglomeration or settling out to hard layer and where there is some settling, redispersion of the oxide can be achieved easily.

We have found that one or more of the problems attending the prior art may be avoided, or at least partially mitigated by comminuting, eg Intensive milling, the oxide in the presence of a liquid being constituted by or including a component having available hydrogen ion and/or oxygen ion.

Figures 1, 2:
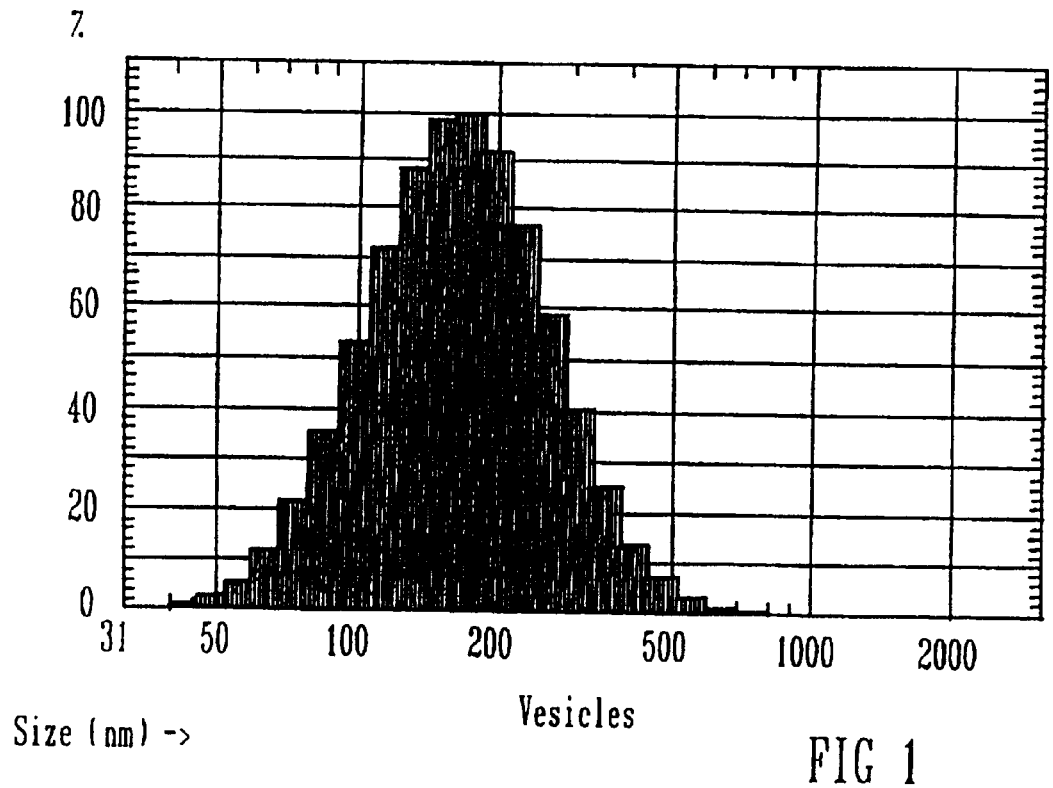
FIG. 1 is a particle size distribution plot towards zinc oxide as prepared by Example 6, showing vesicle size (nm) in the abscissa.
FIG. 2 is a particle size distribution plot towards zinc oxide dispersion as prepared by Example 10, showing solid particle size (nm) in the abscissa.

Accordingly the present invention provides, in one aspect, a process for producing a dispersion of particles of an inorganic oxide selected from zinc oxide, titanium dioxide or iron oxide in a liquid, the process including comminuting the oxide in the presence of the liquid, the liquid being constituted by or including a component having available hydrogen and/or oxygen ions.

Without wishing to limit the invention in any way, it is believed that when zinc oxide crystals are comminuted during the process of the invention, they produce smaller particles with fresh cleavage surfaces, these surfaces when produced by comminution In the liquid, bond to available hydrogen ion and/or oxygen ion to form zinc oxide which is both encapsulated and bonded to a film of the liquid. This gives a very stable product which does not aggregate, agglomerate or settle out to a hard layer.

Preferably the oxide is comminuted to a particle size of less than about 30 $\mu$m. More preferably the oxide Is not comminuted below a particle size of about 0.025 $\mu$m, preferably about 0.04–10 $\mu$m. A comminuted particle size of about 0.04–0.1 $\mu$m is particularly preferred.

The component containing available hydrogen ion and/or oxygen ion may be a substance or compound having one or more hydroxyl groups or hydrogen groups. Preferably the liquid is selected from one of an alcohol, ester, hydrogenated ester or polymer containing hydroxyl group(s) or hydrogen group(s) or mixtures of two or more of the foregoing.

Examples of suitable liquids may be selected from the group consisting of dioctyl phthalate, glycerol mono-oleate, glycerol mono stearate, isopropyl myristitate, diethyl phthalate, propylene glycol dicaprylate/caprate, glycerol tricaprylate/caprate, methyl laurate, methyl oleate and dictl adipate.

Preferably the liquid in which comminution takes place is substantially free of water. More preferably the liquid is free of water.

Comminution of the oxide may be carried out by milling. Milling may be achieved by any suitable method. Milling may be carried out using a ball mill, or other intensive mill such as a bead mill, attritor mill or sigma mixer.

Preferably the process of the invention is carried out by adding the oxide in the particulate form to the liquid whilst milling occurs although the oxide may be combined with the liquid and the mixture milled. The initial particle size of the oxide may be in the range of about 0.1 $\mu$m to 10.0 $\mu$m.

Preferably the oxide is zinc oxide. The zinc oxide used in the present invention may be crystalline zinc oxide. Amorphous porous zinc oxide is preferred where a very small comminuted particle size is desired as it is easier to mill down.

Preferably comminution occurs at an elevated temperature. The elevated temperature may be in the range of about 50° to 15° C. The oxide may added in an amount in the range of about 5% to 95% of the final dispersion.

In a further aspect, the present invention provides a liquid dispersion of an inorganic oxide in particulate form, the oxide selected from zinc oxide, titanium dioxide and iron oxide, wherein the oxide has a particle size in the range of about 0.02–30 $\mu$m and wherein the liquid is constituted by or includes a component having an available hydrogen ion, wherein the surfaces of the oxide particles are bonded to the available hydrogen ions and/or oxygen ions.

The oxide dispersion of the invention may be produced by the process of the present invention.

Preferably the oxide is present in the dispersion in an amount of about 5% to 95% by weight. Preferably the oxide is present in an amount of at least about 10% by weight, more preferably greater than about 20% by weight of the dispersion. The surface area of the particulate oxide in the dispersion may be about 6m$^2$ per gram of oxide to about 50m$^2$/g, more preferably about 20 to about 30m$^2$/g.

Preferably the liquid component of the dispersion is selected from an alcohol, ester, hydrogenated ester or a polymer containing available hydrogen ion, for example, hydroxyl groups or hydrogen groups or mixtures of one or more thereof.

Preferably the dispersion of the oxide includes oxide in a particle range of about 0.4 to 10 $\mu$m, more preferably about 0.04–0.5 $\mu$m.

A zinc oxide powder has a refractive index of 1.9–2 with an oil absorption factor of 32.3. In its natural form. It is one of the whitest pigments available, however when it is milled to a particle size less than 0.1 $\mu$m in the liquid containing available hydrogen ion, it exhibits a distinctive yellow colour. This is believed to be due to scattering of light, similar to the yellow colours in opals which also scatter light with 25 nm crystals.

Preferably the oxide is zinc oxide.

The dispersion of the present invention has a wide range of applications in which its UV absorbent properties may be utilised. In particular, the zinc oxide product of the present invention also has antioxidant properties which also makes it useful in many applications.

The oxide dispersion of the present invention may constitute or be included In topical preparations such as skin care or therapeutic products, cosmetics or hair care products. The dispersion of the invention may be used in coloured cosmetics such as lipsticks, face powders, mascara, eye shadows, blushers etc. The dispersion may also be included In stick products such as an anti-chap stick.

The present invention provides a sunscreen composition, the composition including a zinc oxide dispersion in accordance with the present invention.

By appropriate selection of the oxide loading in the suspension (for example, about 20% to 30% oxide), the dispersion of the invention may be incorporated into aerosol products. The product of the Invention may be incorporated into hair care products to provide UV protection.

The dispersion of the invention also has application in the area of coatings and films. The invention Is particularly suitable in instances where a clear finish is required such as in the case of clear lacquers, varnishes and shellacs. In this case, the zinc oxide acts both as a UV absorber and an antioxidant. In the case of a timber coating product, the zinc oxide acts as a UV absorber and by soaking into the timber grain protects the timber product itself.

The dispersion of the invention may be incorporated into latex coating emulsions.

The present invention also finds application in the area of printing inks and is particularly suitable for natural pigmented inks wherein the-oxide may act as an antioxidant and UV absorber.

The product of the invention may also be incorporated into plastic products to use its antioxidants and/or UV absorbing properties. It may be incorporated into addition polymers such as PVC, and polyolefins or condensation polymers such as polyurethanes. The dispersion of the invention may be incorporated in the injection, blow moulding, casting or extrusion stage.

The present Invention also has application in paints as a UV absorber and/or antioxidant. The Invention also finds particular application in the production automotive finishes such as clear film so as to provide more resistance to scratching and abrasion.

The present invention accordingly extends to the above-mentioned compositions or formulations including an oxide dispersion in accordance with the invention.

In order that the invention may be more readily understand, we provide the following non limiting examples.

METHOD

Zinc oxide, titanium dioxide or ion oxide may all be milled in a liquid including a component having available hydrogen ions. Milling may be carried out an intensive mills such as a ball mill, bead mill, attritor mill, edge runner, Z arm or sigma mixer or the like.

Example 1

1220 g zinc oxide 813 g dried tridecanol

The tridecanol was loaded into a bead mill with 10 mm PSZ ball. Milling was started and the zinc oxide fed into the mill, continuously at a slow feed rate. The temperature was allowed to rise to 50° C. The zinc oxide was milled for about 12 hours to disperse all the zinc oxide and the particle size was checked against a stand. A dispersion of zinc oxide particles of the size less than 0.2 $\mu$m dispersed in tridecanol was produced.

Example 2

1220 g zinc oxide 813 g isopropanol

The isopropanol was loaded into a pre mix tank of a bead mill. Zinc oxide was added slowly and continuously. The pre-mix is fed into a bead mill and mixed for six hours and the particle zinc oxide checked against the standard and a dispersion of zinc oxide particles of the size less than about 0.15 μm dispersed in isopropanol was produced.

Example 3

1120 g zinc oxide 813 g glycerol tricaprylate

The glycerol tricaprylate and zinc oxide were loaded into a pre mix tank. The pro mix was mixed and fed into a triple roll mill. The zinc oxide/glycol tricaprylate dispersion was milled until the particle met the standard after three passes.

Example 4

Coated zinc oxide for use in a polyvinyl chloride compmosition was prepared by intensive bead milling of zinc oxide using small bead of 1 mm diameter. Milling was conducted in dioctyl phthalate until a zinc oxide particle size in the range of from 40 to 70 nm was provided. The coated zinc oxide was used in preparing the polyvinyl chloride composition detailed below.

| Polyvinyl Chloride Composition | Kg |
| --- | --- |
| PVC Resin K-66 | 100 |
| Dioctyl Phthalate | 50 |
| Lubricant Wax | 0.5 |
| Calcium/Zinc Stabiliser | 2.0 |
| 85% Zinc Oxide encapsulated (coated) milled in DOP | 5.0 |

The resin mix composition was run on a double roll mil @180° C. for 3 minutes to give a clear sheet Example 5

Coated zinc oxide was prepared by ball Intensive milling of zinc oxide in the presence of a glycerol tricaprylatelcaprate mixed ester. Milling was conducted in an intensive bead mill using bead of 1 mm diameter at 80° C. until the particle size of about 40–70 nm was provided. The zinc oxide was used in preparing a water based printing varnish detailed below.

| Water Based Printing Varnish | Kg |
| --- | --- |
| Joncryl 74 (acrylic polymer resin) | 55 |
| Emulsion | 32 |
| Jonalec 26 (acrylic polymer resin) | 5 |
| 85% Zinc Oxide Coated | 3 |
| Butyl Cellosolve | 5 |
| | 100.0 |

Mix with high speed mixer

Example 6

Coated zinc oxide was prepared by the method described in Example 5 and used to prepare the oil based printing varnish detailed below.

| Oil Based Printing Varnish | Kg |
| --- | --- |
| Pentalyn 833 (pentaerythritol ester) | 20 |
| Pentalyn 858 (pentaerythritol ester) | 20 |
| Micronised PE Wax | 15 |

| -continued | |
| --- | --- |
| Oil Based Printing Varnish | Kg |
| Micronised PT Wax | 0.5 |
| Long Oil Linseed Alkyd | 15 |
| Megasol 52 Solvent (hydrocarbon solvent) | 26.5 |
| 85% Zinc Oxide Coated | 3 |
| | 100.0 |

Mix with high speed mixer

The zinc oxide particle size distribution (nm) in an example of a dispersion in accordance with the invention has a number-weighted gaussian analysis. (Vesicles) as follows:

| GAUSSIAN SUMMARY: | |
| --- | --- |
| Mean Diameter = 184.8 nm | Chi Squared = 0.103 |
| Stnd. Deviation = 85.6 nm (46.3%) | Baseline Adj. = 0.000% |
| Coeff. of Var'n = 0.463 | Mean Diff. Coeff. = 2.32E-08 cm2/s |

Cumulative Results: 25% of distribution<113.15 nm 50% of distribution<154.51 nm 75% of distribution<211.56 nm 99% of distribution<457.08 nm The distribution may be represented as shown in FIG. 1.

Example 7

Sunscreen Lotion

| Phase A 60° C. Mix until dispersed. | Kg |
| --- | --- |
| Zinc Oxide | 150 |
| "Elafac" (glycerol ester) | 50 |
| "Minno 21" (dispersing agent) | 50 |
| "Bridge 58" (emulsifier) | 3.0 |

Phase A was prepared by milling in a bead mill using 1 mm beads over a period to provide coated zinc oxide particles of size 100 to 400 nm.

| Phase B Blend at 60° C. | |
| --- | --- |
| "Keltanol" Solution (gum suspending agent) | 0.3 |
| "Carbopol" 974 (thickener) | 0.3 |

Phased

"CA24" Preservative 0.2

Procedure

Add Phase B to Phase A. Mix until smooth. Then with Propeller mixer causing vortex add Phase D—mix until uniform.

Example 8

Sunscreen Lotion

| Phase A 40° C. Mix until disperses. | Kg |
| --- | --- |
| Cupl Pic (glycerol ester) | 2.0 |
| Minno 21 dispersing | 10.0 |
| Titanium dioxide (Micronisers) coated | 15.0 |
| Zinc Oxide (Micronisers) coated | 12.5 |

Phase A was prepared by milling the titanium and zinc oxide composition with the ester in a ball mill using beads of size 1 mm diameter to provide a particle size of 100 to 400 nm.

| Phase B 40° C. | |
|---|---|
| Water | 60.3 |
| Phase C Dry blend | |
| Veegum | 0.70 |
| Keltanol | 0.3 |
| Phase D | |
| CA24 Preservative | 0.2 |

The sunscreen composition was prepared by adding. Phase C to Phase B and mixed until the composition was smooth. With proper mixing (Propeller causing a vortex) Phase A was added and the composition missed until uniform. Phase D was then added and the resulting composition mixed until uniform.

The sunscreen lotion provides a high level of UV protection without significant whitening of the skin.

Zinc oxide can be used as a protector for light fastness of cheaper and expensive pigments in printing inks and overprint varnishes. Moreover it protects clear varnishes which degrade in the presence of ultraviolet light.

Example 9

Coating Composition The coated zinc oxide prepared in accordance with Example 5 may be incorporated Into an acrylic emulsion coating composition for use as a timber finish or other coating application.

The milling is conducted in the absence of water and the coated zinc oxide mixture is subsequently dispersed In water. The resulting composition may be used in forming an emulsion with acrylic resin or may be incorporated into a preformed acrylic resin emulsion.

Example 10

The zinc oxide single distribution is an example of a dispersion of the invention for use in coating or printing varnish compositions as shown below and is graphically represented in FIG. 2.

NUMBER-Weighted NICOMP DISTRIBUTION Analysis (Sold Particles)

| NICOMP SUMMARY: | |
|---|---|
| Peak Number 1: Mean Diameter = 80.0 nm | Number: 96.85% |
| Peak Number 2: Mean Diameter = 325.1 nm | Number: 3.15% |

Mean Diameter=90.4 nm Fit Error=2.737 Residual=12.165

| NICOMP SCALE PARAMETERS: | |
|---|---|
| Min. Diam. = 30.0 nm | Plot Size = 45 |
| Smoothing = 3 | Plot Range = 100 |

| | |
|---|---|
| Run Time = 0 Hr 11 Min 15 Sec | Temperature = 20 deg C. |
| Count Rate = 466 Khz | Viscosity = 1.002 cp |
| Channel #1 = 4027.8 K | Index of Ref. = 1.333 |
| Channel Width = 45.0 usec | |

| GAUSSIAN SUMMARY: | |
|---|---|
| Mean Diameter = 165.2 nm | Chi Squared = 4.236 |
| Stnd. Deviation = 64.8 nm (39.2%) | Baseline Adj. = 0.000% |
| Coeff. of Var'n = 0.392 | Mean Diff. Coeff. = 1.22E-08 cm2/s |

What is claimed is:

1. A process for producing a dispersion of particles of an inorganic oxide selected from zinc oxide, titanium dioxide or iron oxide in liquid, the process including comminutng the oxide in the presence of the liquid to produce smaller particles with fresh cleavage surfaces to provide a particle size in the range of from 0.025 to 0.5 $\mu$m, wherein the liquid is selected from the group consisting of alcohols, esters, hydrogenated esters and polymers containing available hydroxyl group(s) and wherein the liquid is free of dispersing agent.

2. A process according to claim 1 wherein the liquid selected from the groups consisting of dioctyl phthalate, glycerol mono-oleate, glycerol mono-stearate, isopropy myristate, diethyl phthalate, propylene glycol dicaprylate/caprate, glycerol tricapylate/caprate, methyl laurate, propylene glycol, methyl oleate, dioctyl adipate and mixtures thereof.

3. A process according to claim 1 wherein the inorganic oxide is comminuted to provide a particle size in the range of from 0.04 to 0.1 $\mu$m.

4. A process according to claim 1 wherein the particles are comminuted in the liquid from a particle size of 0.2 $\mu$m to 10.0 $\mu$m to provide a particle size in the range of 0.04 to 0.1 $\mu$m.

5. A process according to claim 1 wherein the liquid is substantially free of water.

6. A process according to claim 1 wherein the comminuting is carried out using a ball mill, bead mill, attritor mill or sigma mixer.

7. A process according to claim 1 wherein the inorganic oxide is zinc oxide.

8. A process according to claim 1 wherein the comminuting is carried out at a temperature in the range of about 50 to 150° C.

9. A process according to claim 1 wherein the inorganic oxide is added in an amount in the range of 10% to 95% by weight of the final dispersion.

10. A process according to claim 1 wherein the surface area of the particulate inorganic oxide is from about 6m$^2$ per gram of inorganic oxide to about 50m$^2$ per gram.

11. A process according to claim 1 wherein the disperison in incorporated into a topical preparation for use in skin care, therapeutic treatment, a cosmetic or in hair care.

12. A process according to claim 1 wherein a colouring agent is added to the dispersion to provide a cosmetic formulation.

13. A process according to claim 1 wherein the dispersion is incorporated into a cosmetic selected from the group consisting of lipstick, face powder mascara, eye shadow and blush.

14. A process according to claim 1 wherein the inorganic oxide is zinc oxide present in an amount of from 20 to 30% by weight of the composition and the dispersion is used in manufacture of a sunscreen.

15. A process according to claim 1 wherein the dispersion is incorporated into a composition selected from the group consisting of a coating and plastics composition.

16. The process according to claim 15 wherein the composition is semi transparent.

17. The process according to claim 15 wherein the composition is clear.

* * * * *

UNITED STATES PATENT AND TRADEMARK OFFICE
CERTIFICATE OF CORRECTION

PATENT NO. : 6,083,490
DATED : July 4, 2000
INVENTOR(S) : David Graham Ellis et al.

It is certified that error appears in the above-identified patent and that said Letters Patent is hereby corrected as shown below:

Column 8, line 12, "comminutng" should be "comminuting".

Column 8, line 54, please insert a comma "," between "face powder" and "mascara".

Signed and Sealed this

First Day of May, 2001

Attest:

NICHOLAS P. GODICI

Attesting Officer

Acting Director of the United States Patent and Trademark Office